United States Patent [19]

Falk et al.

[11] Patent Number: 5,191,212

[45] Date of Patent: Mar. 2, 1993

[54] ANALYTICAL SYSTEM WITH ELECTROTHERMAL ATOMIZER AND MASS SPECTROMETER FOR ATOMIC AND MOLECULAR ANALYSIS

[75] Inventors: Heinz Falk, Kleve; Hermann Wollnik, Fernwald, both of Fed. Rep. of Germany

[73] Assignee: Spectro GmbH, Kleve, Fed. Rep. of Germany

[21] Appl. No.: 719,127

[22] Filed: Jun. 20, 1991

[30] Foreign Application Priority Data

Jul. 11, 1990 [DE] Fed. Rep. of Germany ....... 4022061

[51] Int. Cl.$^5$ ..................... G01N 21/73; G01N 21/74
[52] U.S. Cl. .................... 250/288; 250/287; 356/312
[58] Field of Search ............... 250/287, 288; 356/312, 356/244

[56] References Cited

U.S. PATENT DOCUMENTS

| | | | |
|---|---|---|---|
| 4,529,307 | 7/1985 | Holcombe et al. | 356/312 |
| 4,729,656 | 3/1988 | Churchill et al. | 356/312 |
| 4,833,322 | 5/1989 | Forster et al. | 250/288 |
| 4,895,443 | 1/1990 | de Loos-Vollebeiyt | 356/36 |
| 4,948,962 | 10/1990 | Mitsui et al. | 250/288 |
| 4,955,717 | 9/1990 | Henderson | 356/316 |
| 5,065,018 | 11/1991 | Bechtold et al. | 250/287 |
| 5,144,127 | 9/1992 | Williams et al. | 250/287 |

FOREIGN PATENT DOCUMENTS 3718244 8/1988 Fed. Rep. of Germany.

OTHER PUBLICATIONS

Rapid Communications in Mass Spectrometry, R. Grix, vol. 2, No. 5, 1988, A Time-of-Flight Mass Analyzer with High Resolving Power.
CRC Critical Reviews in Analytical Chemistry, H. Falk, vol. 19, No. 1988, NY, pp. 29-64.
Journal of Applied Physics, vol. 64, No. 5, Sep. 1988, NY pp. 2271-2278.
A Time-of-Flight Mass Analyzer with High Resolving Power-R, Grix et al., Rapid Communications in Mass Spectrometry, vol. 2, No. 5, 1988, pp. 83-88.
Graphite Furnaces as Atomizers and Emission Sources in Analytical Atomic Spectrometry, Heinz Falk, vol. 19, Issue 1 (1988) pp. 29-64.

Primary Examiner—Jack I. Berman
Assistant Examiner—James Beyer
Attorney, Agent, or Firm—Herbert Dubno; Yuri Katzshov

[57] ABSTRACT

The analytical system for measuring the concentrations of elemental or molecular constituents of an existing solid, liquid or aerosol sample, the sample being dried by an electrothermal atomizer, reduced to ashes, if necessary, vaporized, the sample vapor ionized, the resulting ions supplied during a short time in comparison with the storage time to a preferably simultaneously operating mass spectrometer, and the frequency of the respective ion masses being measured.

17 Claims, 2 Drawing Sheets

ANALYTICAL SYSTEM WITH ELECTROTHERMAL ATOMIZER AND MASS SPECTROMETER FOR ATOMIC AND MOLECULAR ANALYSIS

FIELD OF THE INVENTION

The invention relates to a new analytical system for determining the quantitative concentration of the constituents of solid, liquid or aerosol samples, preferably in the trace range, by use of an electrothermal analyzer (ETA) in connection with a mass spectrometer (MS).

BACKGROUND OF THE INVENTION

The analytical system is designed to ensure a reduced sample requirement in the microliater-range, low absolute detection limits up to below the pg-range, a high dynamic range of the analytical signal, and small trace determination errors due to the main constituents of the sample.

It is known that mass spectrometers can be used for the elemental analysis of solid samples by application of a spark ionization MS, or a glow discharge in connection with an MS, U.S. Pat. No. 4,794,252, and that the analysis of liquid and aerosol samples by means of inductively coupled plasma, ICP-MS, is possible. Spark mass spectrometers and glow discharge mass spectrometers are expensive and time-consuming systems and not suitable for the analysis of liquid or aerosol samples. An ICP-MS requires, because of the ICP which is operated at atmospheric pressure, high pumping capacities for a differential pumping system in order to maintain a high vacuum in the MS. Both the introduction of the sample through an atomizing system and the transfer of the ions from the ICP to the MS are highly inefficient, and this restricts the detection sensitivity and requires relatively high sample quantities in the ml-range.

The introduction of dried aerosols of the analytical sample in an MS is known, U.S. Pat. No. 4,403,147. Such systems require a carrier gas stream for the transport of the aerosol, and thus also high pumping capacities, similar to the ICP-MS. The atomization and ionization of the aerosol causes high additional cost in order to achieve an acceptable efficiency.

In usual quadrupole mass spectrometers, i.e. in ICP-MS at present, only ions of a certain ionic mass are recorded at any time, whereas the ions of all the other masses are lost. The same applies also to sector-field mass spectrometers with a single exit slit. In both cases, only 0.1% or 0.01% of the ions which have been formed at one time, contribute typically to the intensity recorded in the spectrum. However, if it is possible to store for a while all the ions formed over a longer period in a storage unit prior to the mass analysis, and to use a mass spectrometer with simultaneous mass detection, all or at least a very high percentage of all the ions which have been formed at one time are also detected.

It is known from atomic absorption spectrometry that extremely high atomization efficiencies can be achieved with electrothermal atomizers.(H.F. Falk, CRC Critical Reviews 19, Issue 1, p. 29-64, New York, 1988). These atomizers are operated, however, at atmospheric pressure and not suitable in this form for coupling to an MS.

Various realizations of ion traps based both on electromagnetic and electrostatic effects are known. Furthermore, combinations of time-of-flight mass spectrometers and ion traps have also been realized. ("Rapid Communications in Mass Spectrometry, 2, 1988, 83-85).

These systems are, however, not suitable because of their design for the analysis of solid, liquid or aerosol samples.

In ion traps, an appropriate control system makes it possible to use the trap first as storage unit, and subsequently as mass analytical system. If a separate storage unit is provided, the ion can be injected after extraction into any mass spectrometer, i.e. also into a quadrupole spectrometer or a sector-field mass analyzer. A further advantage of time-of-flight mass spectrometers is the possibility of ensuring that the ions of various masses start approximately simultaneously (or after exactly defined mass-dependent periods). This "simultaneous" start can be achieved by concentrating the period in which the stored ions are released (about 1 microsec) after an acceleration path to considerably shorter times (about 10 nsec), similar to the klystron bunching. This results, however, in a substantial increase of the energy width of the ion distribution, so that the time-of-flight mass spectrometer has to be relatively highly energy isochronous. This means that the ions of a mass, which have slightly varying energies, have to feature the same time of flight, this being achieved by ensuring that the higher energy ions can reach the detector only via an appropriately designed detour, e.g. by providing an ion reflector, into which the higher energy ions penetrate to a greater depth.

OBJECTS OF THE INVENTION

It is therefore a principal object of the invention to provide an analytical system, which enables an analysis of the elemental and molecular constituents of solid, liquid or aerosol samples with the high detection sensitivity typical for mass spectrometry, without requiring high pumping capacities for a differential pumping system between sample introduction and the MS.

Still another object is to provide the method for measuring the concentration of elemental and molecular constituents of a sample avoiding drawbacks characteristic to the prior art.

This task is achieved according to the invention by vaporizing the sample to be analyzed after a thermal pretreatment in vacuum, ionizing it in an ionizer, storing the resulting ions and feeding the latter during a short time in comparison with the storage time to a preferably simultaneously measuring MS, in order to determine the respective frequencies of the ions.

Such a stored ion source can be designed according to the electron-impact ionization principle (U.S. Pat. No. 4,904,872), the gas mixtures being analyzed thus with a high sensitivity in combination with a time-of-flight mass spectrometer.

The sample can be introduced in the ETA in the known manner as briquetted solid matter, by means of a microliter dosing unit or impactor for moist or dry aerosols.

In order to limit the disturbing effect of the main components of the sample on the measurement of trace constituents, the temperature of the ETA can be controlled in such a manner that the vaporization of both parts is timely separated that the ionizer and/or ion storage unit are switched off during the vaporization of the main components. In this way, neither the capacity of the ion trap, nor that of the ion detector, is affected by the main components.

By coupling the temperature control system of the ETA with the measuring signal of the MS it is possible to achieve an optimal heating rate and to prevent any over-range of the MS.

Under these conditions, a modulation of the ionization energy is also possible. This mode of operation can be used for an alternate measurement of atomic and molecular constituents.

The analytical system according to the invention offers the advantage of higher detection sensitivity in the picogram range and up to the femtogram range, and reduces at the same time the amount of equipment required by eliminating the differential pumping system. Besides, measuring errors due to matrix effects are minimized.

BRIEF DESCRIPTION OF THE DRAWING

The above and other objects, features and advantages of our invention will become more readily apparent from the following description, reference being made to the accompanying highly diagrammatic drawing in which.

SPECIFIC DESCRIPTION

Figure 1:
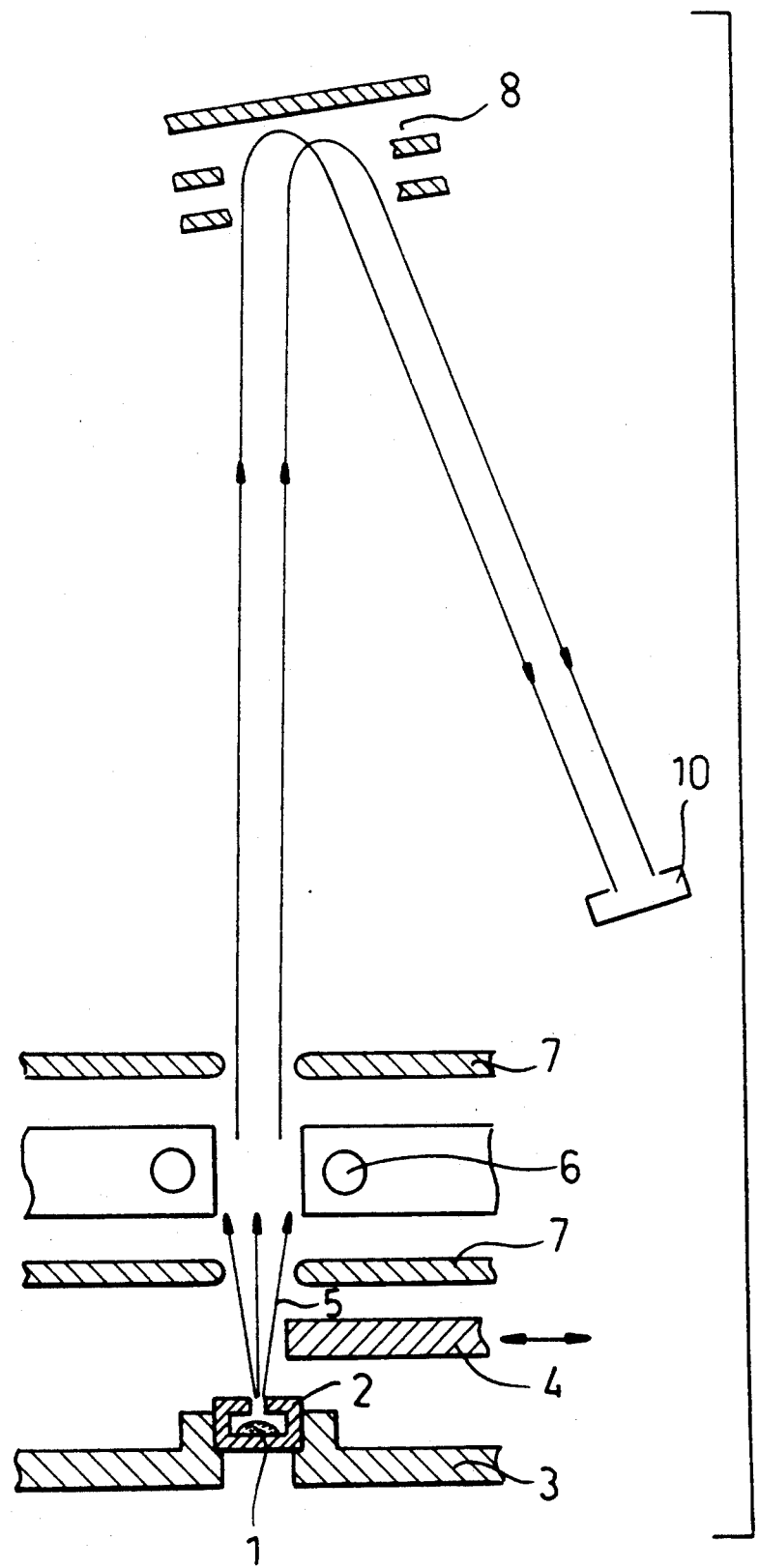
FIG. 1 shows an embodiment of the invention.
Figure 3:
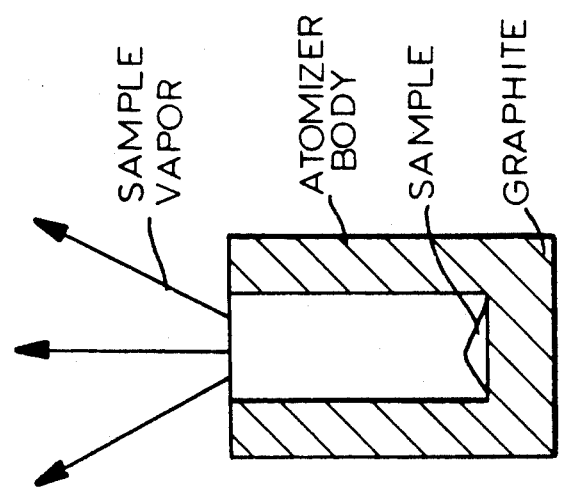
FIGS. 2 and 3 show cylindrically and conically shaped atomizers with open ends.
Figure 2:
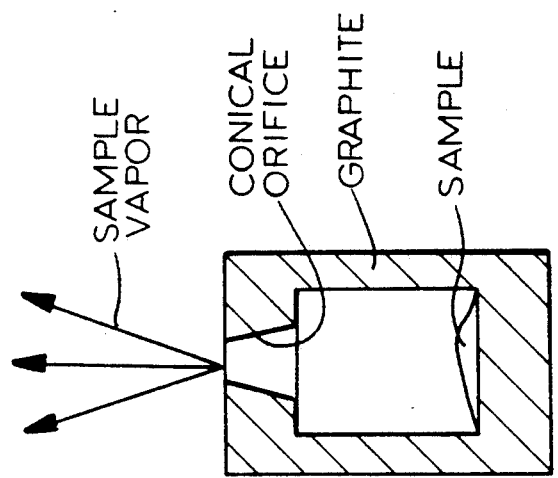

The drawing represents an embodiment of the system according to the invention with the use of a time-of-flight MS. The entire system is arranged in a high-vacuum vessel 50, the design of which is not determining for the operation of the system and therefore not included in the drawing.

Sample 1 is introduced in the ETA sample vessel 2 while the vacuum lock 4 isolates the atomizer from the rest of the system. The atomizer provided with heating means for reducing the sample to ashes. As a rule, the atomizer is composed of an element selected from the group consisting of graphite or ceramic material and at least partially coated with pyrolytic carbon. As a variant, the atomizer may be composed of a high-melting metal. The sample can be pretreated now by heating the sample vessel 2, e.g. by means of an electric voltage applied to the electrodes 3, or else by microwaves or laser beam. If necessary, the ETA can be swept by a protective gas during the pretreatment of the sample. The structure of the atomizer is well known and can have an end receiving the sample vessel. A shape of the tube extending between opposite ends of the atomizer varies from cylindrical, to cuboid to pyramid cross section and, of course, is a hollow body. In case of using mechanical means for introducing the sample vessel, the atomizer is provided with a receiving part which is easily replaceable. The part of the vacuum equipment which contains the ETA can be evacuated after completed pretreatment of the sample, and the vacuum lock can be opened. Heating of the ETA by voltage application to 3, or by microwaves or laser beam irradiation, leads to vaporization, i.e. atomization, of the sample constituents. The vapor moves inside a cone 5 defined by the nozzle-shaped outlet of the ETA in the direction of the ionizer 6. The ions formed in this way reach the ion storage unit 7, which is preferably designed as electrostatic potential well, the potential well being either static or pulsating, similarly to an ion trap.

The ions are extracted then after a certain collecting time from the storage unit, longitudinally concentrated similarly to a klystron, and supplied to a largely energy-isochronous time-of-flight mass spectrometer, which includes an ion reflector 8. The times of flight, which vary because of the different masses, are detected then by an ion detector.

The liquid or solid sample can be introduced externally into the atomizer and the entire atomizer introduced through a vacuum lock into the analytical system.

We claim:

1. A method of measuring the concentration of elemental and molecular constituents of a sample including nonselected components and other components to be determined, said method comprising the steps of:
   (a) thermally pretreating a sample in an electrothermal atomizer at a first temperature to vaporize and to drive off nonselected components of the sample;
   (b) thereafter heating the sample to a vaporization temperature of other components, thereby turning the other components to atomized components thereby forming an atomic beam;
   (c) ionizing the atomized components downstream of the atomic beam while conveying the atomized components along the path;
   (e) thereafter collecting ions of the atomized components in an ion trap for a first period of time; and
   (f) thereafter emitting simultaneously the ions from the trap over a second period of time shorter than the first period of time, and supplying the ions to a mass spectrometer for measuring abundance of respective masses of the ions by the mass spectrometer thereby measuring the concentration of constituents of the sample.

2. The method defined in claim 1 wherein said step (f) includes reflecting said plurality of ions from a reflector located downstream of the ion trap.

3. The method defined in claim 2 wherein said step (b) includes a step of controlling a heating rate of the electrothermal atomizer, said rate being selected so that a number of the ions of said other components remains within preselected limits.

4. The method according to claim 1 wherein a liquid or solid sample is introduced under atmosphere pressure into an atomizer and that the entire atomizer is introduced through a vacuum lock into the analytical system.

5. An analytical system for measuring the concentration of elemental and molecular constituents of a sample including nonselected components and other components to be determined, said sample being a solid, liquid or aerosol sample, said analytical system comprising:
   an electrothermal atomizer for selectively heating the sample introduced into said atomizer to a first temperature for vaporization and driving off of nonselected components and to a second temperature corresponding to vaporization of the other components to be analyzed;
   a vacuum lock connected with said atomizer for controllably isolating said atomizer during heating of said sample to said first temperature, the other components being turned into a gaseous state and conveyed along a path in a flow direction thereof upon heating said sample at said second temperature;
   ionizing means for forming a plurality of ions of said other components downstream of said vacuum lock in said flow direction;
   ion storage means for collecting said plurality of ions downstream of said lock for a first period of time, said lock being open during heating said sample to said second temperature;

means for simultaneously releasing said plurality of ions from said ion storage means; and a mass spectrometer downstream of said storage means in said flow direction, said spectrometer measuring abundance of the respective masses of said plurality of ions delivered thereto for a second period of time shorter than said first period.

6. The system defined in claim 5, further comprising delivering means for introducing said sample into said atomizer.

7. The system defined in claim 6 wherein said delivering means includes a gas stream, the sample being liquid or solid aerosol introduced into said atomizer through said gas steam.

8. The system defined in claim 5 wherein said atomizer is a beam source, said source being atomic or molecular beam source extending along an axis directed towards said ionizing means.

9. The system defined in claim 5 wherein said atomizer is composed of an element selected from the group consisting of graphite, ceramic or pyrolytic carbon.

10. The system defined in claim 5 wherein said atomizer is composed of a high-melting metal.

11. The system defined in claim 5 wherein said atomizer is formed with a part provided with an open end receiving said sample, said part being cylindrical or conical hollow body.

12. The system defined in claim 11 wherein said part is replaceable.

13. The system defined in claim 5 wherein said mass spectrometer is a sector-field mass spectrometer.

14. The system defined in claim 5 wherein said mass spectrometer measures a time of flight of said plurality of ions.

15. The system defined in claim 5 wherein said ionizing means includes a microwave or photoionization unit.

16. The system defined in claim 5 wherein said atomizer is housed in a first vacuum vessel, said first vacuum vessel being isolated from a second vacuum vessel receiving said ionizing means, storage means and mass spectrometer by a vacuum lock to be opened before the said second vaporization temperature.

17. The system defined in claim 5, further comprising a sample vessel containing the sample to be analyzed and mounted in said atomizer.

* * * * *